(12) United States Patent
Fumiyama

(10) Patent No.: US 10,405,837 B2
(45) Date of Patent: Sep. 10, 2019

(54) PUNCTURE NEEDLE UNIT AND PUNCTURE NEEDLE DEVICE, AND SAFETY TUBE FOR SAME

(71) Applicant: Hideo Fumiyama, Tokyo (JP)

(72) Inventor: Hideo Fumiyama, Tokyo (JP)

( * ) Notice: Subject to any disclaimer, the term of this patent is extended or adjusted under 35 U.S.C. 154(b) by 275 days.

(21) Appl. No.: 15/520,677

(22) PCT Filed: Oct. 20, 2015

(86) PCT No.: PCT/JP2015/079541
§ 371 (c)(1),
(2) Date: Apr. 20, 2017

(87) PCT Pub. No.: WO2016/063862
PCT Pub. Date: Apr. 28, 2016

(65) Prior Publication Data
US 2017/0290573 A1    Oct. 12, 2017

(30) Foreign Application Priority Data
Oct. 22, 2014   (JP) .................................. 2014-215120

(51) Int. Cl.
*A61B 5/00*     (2006.01)
*A61B 10/02*    (2006.01)
(Continued)

(52) U.S. Cl.
CPC .......... *A61B 10/0233* (2013.01); *A61B 5/153* (2013.01); *A61B 5/15003* (2013.01);
(Continued)

(58) Field of Classification Search
CPC .......... A61B 10/02; A61B 17/34; A61B 5/32; A61B 5/150488; A61B 10/0233;
(Continued)

(56) References Cited

U.S. PATENT DOCUMENTS

| | | | | |
|---|---|---|---|---|
| 5,147,327 A | * | 9/1992 | Johnson | A61M 5/3243 604/198 |
| 2003/0229316 A1 | * | 12/2003 | Hwang | A61M 5/3269 604/263 |

(Continued)

FOREIGN PATENT DOCUMENTS

| | | |
|---|---|---|
| JP | 2011-504401 A | 2/2011 |
| JP | 2012-504469 A | 2/2012 |

(Continued)

OTHER PUBLICATIONS

PCT/ISA/210, "International Search Report for International Application No. PCT/JP2015/079541" dated Jan. 19, 2016.

(Continued)

*Primary Examiner* — Eric J Messersmith
(74) *Attorney, Agent, or Firm* — Manabu Kanesaka

(57) ABSTRACT

A biopsy needle unit includes a biopsy needle and an elastically deformable safety tube for partially covering the biopsy needle inserted to a lumen extending in a longitudinal direction. A marker is arranged on the biopsy needle at a position protruding from an end portion of the safety tube on an opposite side of a needle tip of the puncture needle when the needle tip portion is accommodated in the lumen. The safety tube has portions in which the lumen is curved at least partially with respect to the longitudinal direction so that the safety tube is elastically deformed due to contact between an inner circumferential face of the lumen and an outer circumferential face of the biopsy needle when the biopsy needle is inserted to the lumen to cause frictional resistance between the inner circumferential face of the lumen and the outer circumferential face of the biopsy needle.

7 Claims, 16 Drawing Sheets

(51) Int. Cl.
*A61B 17/34* (2006.01)
*A61M 5/32* (2006.01)
*A61B 10/04* (2006.01)
*A61B 5/15* (2006.01)
*A61B 5/153* (2006.01)
*A61B 5/154* (2006.01)
*A61B 17/3205* (2006.01)

(52) U.S. Cl.
CPC .. *A61B 5/150389* (2013.01); *A61B 5/150488* (2013.01); *A61B 5/150511* (2013.01); *A61B 5/150572* (2013.01); *A61B 5/150633* (2013.01); *A61B 5/150725* (2013.01); *A61B 5/150732* (2013.01); *A61B 10/02* (2013.01); *A61B 10/0283* (2013.01); *A61B 10/04* (2013.01); *A61B 17/3403* (2013.01); *A61M 5/3243* (2013.01); *A61B 5/154* (2013.01); *A61B 17/3205* (2013.01); *A61B 17/3478* (2013.01); *A61B 17/3496* (2013.01); *A61B 2010/045* (2013.01); *A61B 2017/3413* (2013.01)

(58) Field of Classification Search
CPC . A61B 10/0283; A61B 17/3403; A61B 10/04; A61B 5/15003; A61B 5/150389; A61B 5/150511; A61B 5/150572; A61B 5/150633; A61B 5/150725; A61B 5/150732; A61B 5/153; A61B 17/3205; A61B 17/3478; A61B 17/3496; A61B 2010/045; A61B 2017/3413; A61B 5/154; A61M 5/32; A61M 5/3243

See application file for complete search history.

(56) References Cited

U.S. PATENT DOCUMENTS

| | | |
|---|---|---|
| 2009/0157013 A1 | 6/2009 | Wong |
| 2012/0116306 A1 | 5/2012 | Heald et al. |
| 2012/0220956 A1 | 8/2012 | Kuracina et al. |

FOREIGN PATENT DOCUMENTS

| | | |
|---|---|---|
| JP | 2012-509747 A | 4/2012 |
| JP | 2012-519511 A | 8/2012 |
| JP | 2014-514010 A | 6/2014 |

OTHER PUBLICATIONS

"bnxTM System", Beacon Endoscopic, searched Jun. 14, 2014, Internet <URL: http://bnxsafety.com/bnx-system/>.

\* cited by examiner

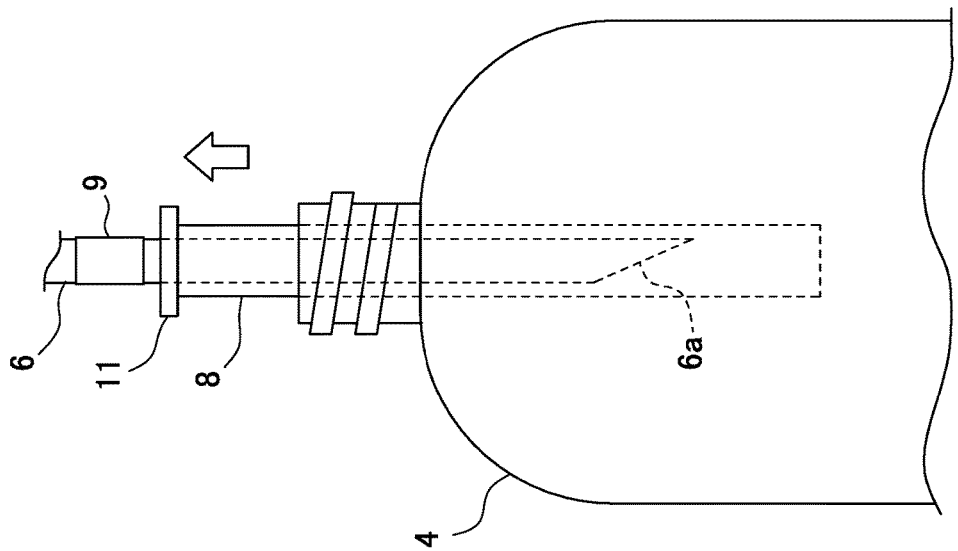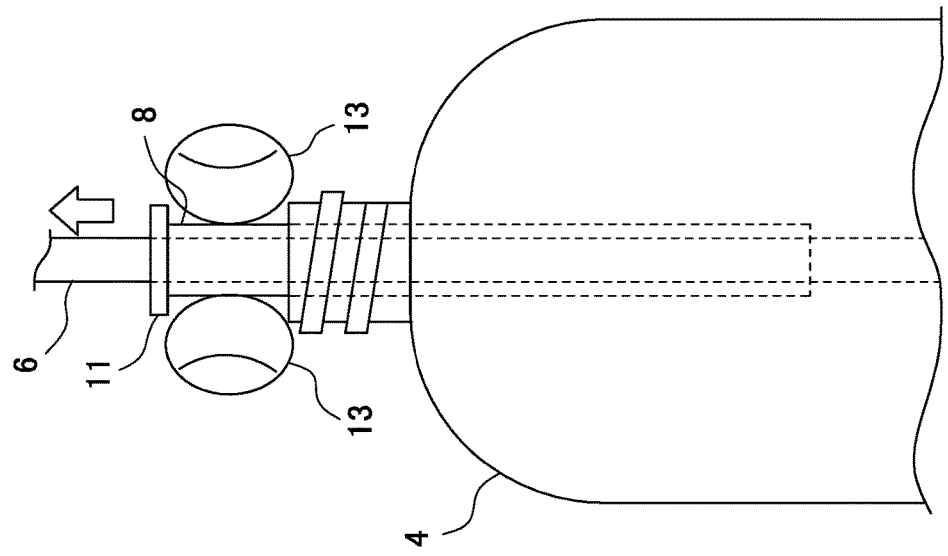

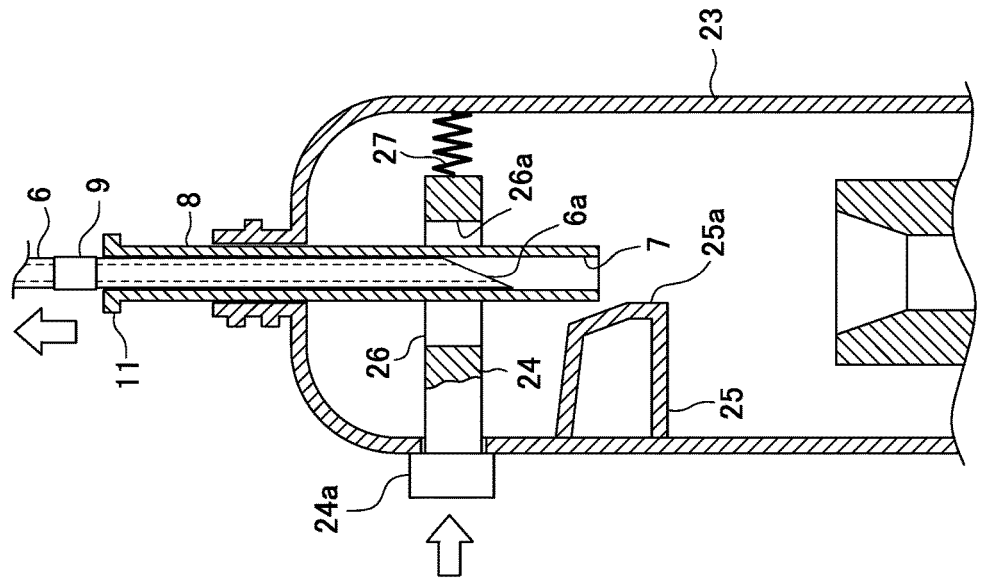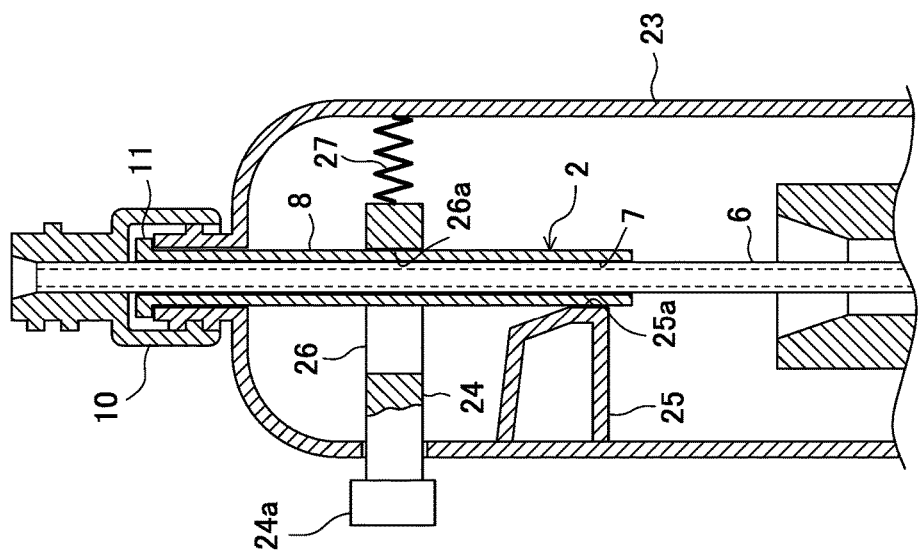

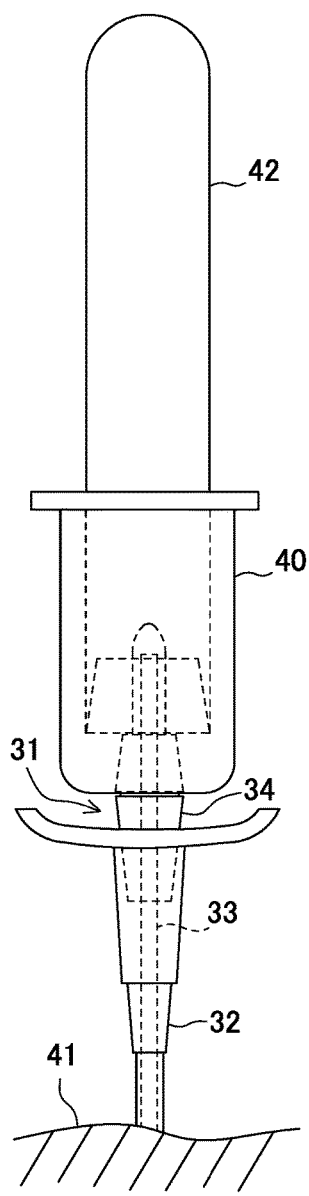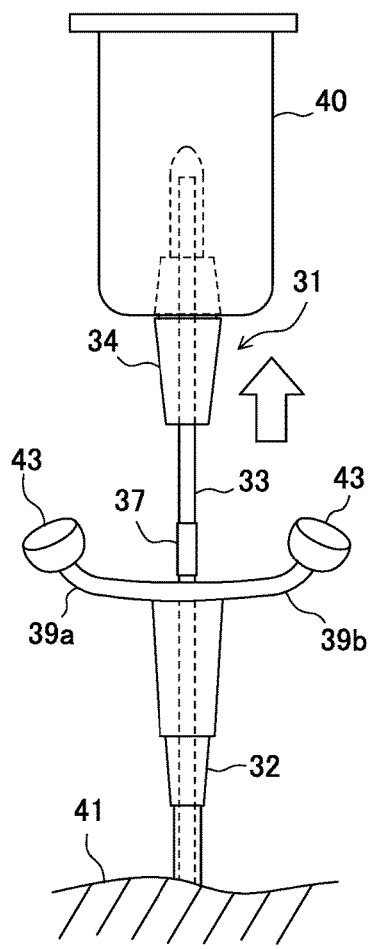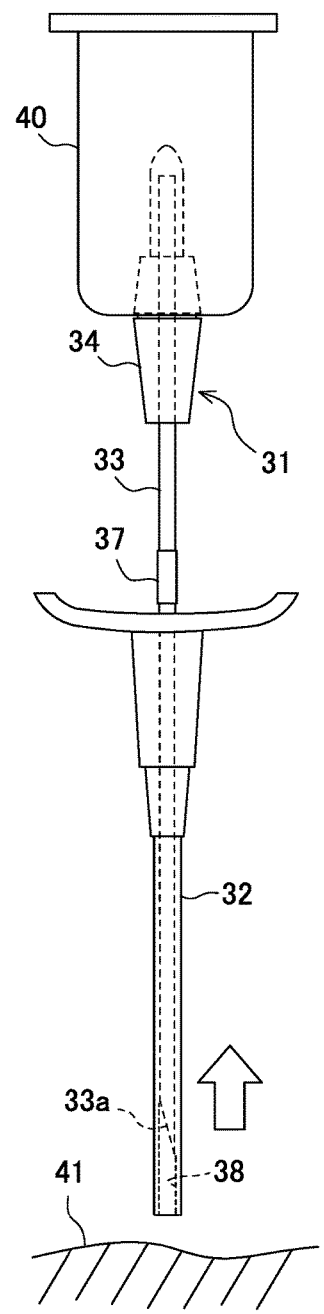

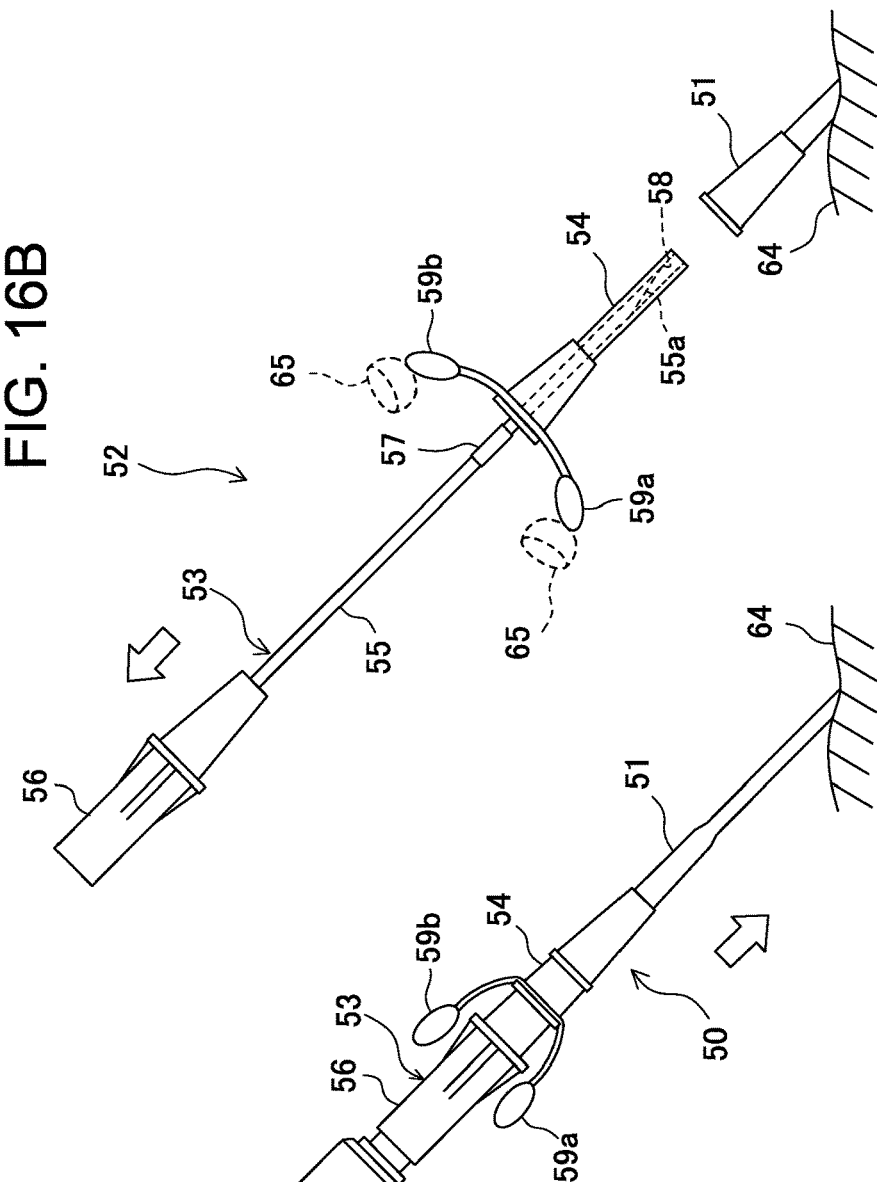

PUNCTURE NEEDLE UNIT AND PUNCTURE NEEDLE DEVICE, AND SAFETY TUBE FOR SAME

RELATED APPLICATIONS

The present application is National Phase of International Application No. PCT/JP2015/079541 filed Oct. 20, 2015, and claims priority from Japanese Application No. 2014-215120, filed Oct. 22, 2014, the disclosure of which is hereby incorporated by reference herein in its entirety.

TECHNICAL FIELD

The present invention relates to a puncture needle unit used for blood sampling, fluid transfusion, and blood transfusion to collect subject biomedical tissue, for example, and a puncture needle device including the puncture needle unit, and further relates to a safety tube to be used for a puncture needle thereof.

BACKGROUND ART

Conventionally in a pathological diagnosis, biopsy has been performed to puncture an alimentary canal and the like of a living body such as a human body with a biopsy needle and to collect tissue as a sample. Particularly, recently, endoscopic ultrasonic fine needle aspiration biopsy (EUS-FNA) in which tissue is collected from an alimentary canal by sticking with a biopsy needle while inserting an ultrasonic endoscope to the alimentary canal and observing an ultrasonic image is widely adopted as a method being less invasive and having high proper diagnosis rate.

Since a tip of a biopsy needle used for EUS-FNA is extremely sharp, there is a risk to prick and hurt a body of a medical staff such as an operator and a caregiver or a patient by accident at the time of removing from the biopsy needle device after collecting tissue. To prevent such an accident, there has been known a needle biopsy device in which removing is performed while having a tip of a biopsy needle accommodated in a sheath (e.g., see Patent Literature 1). Further, there has been proposed a needle protection adapter in which a removed biopsy needle is to be accommodated in a needle protection shaft (e.g., see Patent Literature 2).

Further, a puncture fine-needle aspiration biopsy device constructed of a needle protector including a safety sheath to accommodate a biopsy needle and an adapter for mounting of the needle protector has been commercially available (e.g., see Non-Patent Literature 1). The needle protector is to be automatically locked with the adapter when a biopsy needle is inserted and to be automatically unlocked with the adapter after the biopsy needle is accommodated in the safety sheath when the biopsy needle is pulled out.

CITED LITERATURE

Patent Literature

Patent Literature 1: Japanese Unexamined Patent Application Publication No. 2012-504469

Patent Literature 2: Japanese Unexamined Patent Application Publication No. 2012-509747

Non-Patent Literature

Non-patent Literature 1: "bnxTM System", Beacon Endoscopic, searched Jun. 14, 2014, Internet <URL: http://bnx-safety.com/bnx-system/>

SUMMARY OF THE INVENTION

However, the abovementioned related art has following problems. The needle biopsy device disclosed in Patent Literature 1 has a taper portion, a sphere portion with soldering, adhesive, or the like, or a series of barbed portion formed on a needle tube of the biopsy needle to apply frictional resistance between the biopsy needle and the sheath. Processing with high accuracy is required for such a special needle to apply necessary and sufficient frictional resistance, to cause difficult manufacturing and high cost.

The conventional device disclosed in Patent Literature 2 requires a dedicated needle protection adapter having a complex structure. Particularly, the puncture fine-needle aspiration biopsy device of Non-Patent Literature 1 requires a dedicated adapter for mounting of the needle protector capable of being locked and unlocked. Accordingly, in either case, the whole device becomes extremely expensive.

Similarly, even with a blood sampling needle to puncture a blood vessel and perform blood sampling or a puncture needle for blood access for fluid transfusion or blood transfusion to a blood vessel, there is a risk to prick and hurt a body of a medical staff such as an operator and a caregiver or a patient with a sharp needle tip at the time of removing the needle and a risk of infection owing thereto. Accordingly, it has been demanded to previously and reliably prevent such an accident.

An object of the present invention is to provide an inexpensive puncture needle enabling a puncture needle to be handled safely and easily in a percutaneous procedure such as blood sampling, fluid transfusion, and blood transfusion or EUS-FNA, and a safety tube suitable to be used with the puncture needle.

In addition, an object of the present invention is to provide a puncture needle unit and a safety tube with which a conventional puncture needle device or another conventional device can be used as it is without requiring a dedicated adapter of other equipment having a special mechanism.

Further, the object of the present invention is to provide an inexpensive puncture needle device including such a puncture needle unit and/or safety tube.

The puncture needle unit of the present invention is intended to achieve the above objects comprising a puncture needle, and a safety tube including a lumen which extends throughout a whole length in a longitudinal direction and being capable of elastically deforming to partially cover the puncture needle inserted to the lumen, wherein the puncture needle includes a needle tube having a marker arranged at a position protruding from an end portion of the safety tube on an opposite side of a needle tip of the puncture needle when the needle tip is accommodated in the lumen, and the lumen is curved at least partially with respect to the longitudinal direction so that the safety tube is elastically deformed due to contact between an inner circumferential face of the lumen and an outer circumferential face of the needle tube when the puncture needle is inserted to the lumen to cause frictional resistance between the inner circumferential face of the lumen and the outer circumferential face of the needle tube.

Owing to the frictional resistance generated between the inner circumferential face of the lumen and the outer circumferential face of the needle tube as described above, the safety tube is held at a position on the puncture needle without dropping from the puncture needle with self-weight. Accordingly, by pulling out the puncture needle while holding the safety tube with a finger or a separate device, for example, after integrating the puncture needle unit to a puncture needle device, a device, or the like, it is possible to acknowledge that the needle tip thereof is pulled out to a position accommodated in the lumen with the marker coming out from the end portion of the safety tube.

At this time, by releasing the safety tube from the held state, the safety tube and the puncture needle can be pulled out together due to frictional resistance between the inner circumferential face of the lumen and the outer circumferential face of the needle tube. Accordingly, in EUS-FNA or a percutaneous procedure such as blood sampling, fluid transfusion, and blood transfusion, for example, there is no risk to prick and hurt a body of a medical staff such as an operator and a caregiver or a patient, and safety is secured. Further, such a safety tube can be easily manufactured at low cost with plastic material, for example, so that the cost of the puncture needle unit can be significantly reduced.

In one embodiment, the safety tube is formed by thermoplastic deformation of a tube member of a thermoplastic material including the lumen extending straight in the longitudinal direction. Thus, the safety tube used for the puncture needle unit of the present invention can be easily manufactured at low cost and the cost of the puncture needle unit and the puncture needle device can be reduced.

In another embodiment, the safety tube has a protruding portion protruded outward in a radial direction at an end portion on an opposite side of the needle tip of the puncture needle inserted to the lumen. By engaging the protruded portion at a predetermined position of the puncture needle device or another device or holding the protrude portion with a finger or the like at the time of integrating the puncture needle to the puncture needle device or the other device, the safety tube can be held at a predetermined position and the puncture needle can be inserted and pulled-out more easily.

In another embodiment, the puncture needle is a biopsy needle, and therefore, collecting of subject biomedical tissue can be performed safely and easily.

In another embodiment, the puncture needle is a blood sampling needle, and therefore, blood sampling from a living body can be performed safely and easily.

In further another embodiment, the puncture needle is a puncture needle for blood access and therefore fluid transfusion and blood transfusion to a living body can be performed more safely and easily.

According to another aspect of the present invention, a safety tube is provided including a lumen which extends throughout a whole length in a longitudinal direction to insert a puncture needle, wherein the puncture needle has enough length to cover a needle tip portion of the puncture needle capable to appear and disappear from a tip of the lumen when the puncture needle is moved in an inserting and pulling-out direction in the lumen, and the lumen has a portion protruded inward in a radial direction, is curved at least partially with respect to the axis line direction, elastically deforms outward in the radial direction in contact with an outer circumferential face of the puncture needle inserted to the lumen at the portion protruding inward in the radial direction, and is formed with an elastically deformable material so that frictional resistance is generated between the contacting outer circumferential face of the puncture needle. The safety tube of the present invention is capable of being used in wide range for various puncture needles and provides easily and inexpensively safety of a medical staff and/or patient in the use of the puncture needle.

In one embodiment, the safety tube can be formed by thermoplastic deformation of a tube member of a thermoplastic material including the lumen extending straight in the longitudinal direction. Accordingly, the safety tube can be provided inexpensively in wide range for various puncture needles.

Further, according to another aspect of the present invention, a puncture needle device is provided comprising the puncture needle unit for biopsy according to claim 3 and a main body portion having the puncture needle unit integrated therein, wherein the main body portion includes a sheath for inserting the puncture needle, and a handle portion which holds the safety tube at a predetermined position when the puncture needle is inserted to the sheath. Accordingly, at EUS-FNA, since there is no risk to prick and hurt a body of a medical staff or a patient with the needle tip of the puncture needle in accident, safety of the puncture needle device is improved while achieving cost reduction.

BRIEF DESCRIPTION OF THE DRAWINGS

FIGS. 5A and 5B are partial enlarged views illustrating a process of pulling out the biopsy needle from a handle portion.

FIGS. 9A and 9B are partial enlarged views illustrating a process of pulling out a biopsy needle from a handle portion in a modified example of a biopsy needle device.

FIGS. 12A to 12C are views sequentially illustrating usage of the blood sampling needle unit of FIG. 10.

FIGS. 16A and 16B are views sequentially illustrating usage of the puncture needle system of FIG. 13.

EMBODIMENTS OF THE INVENTION

In the following, a biopsy needle unit and a biopsy needle device of the present invention will be described in detail based on preferable embodiments with reference to the attached drawings.

Figure 1:
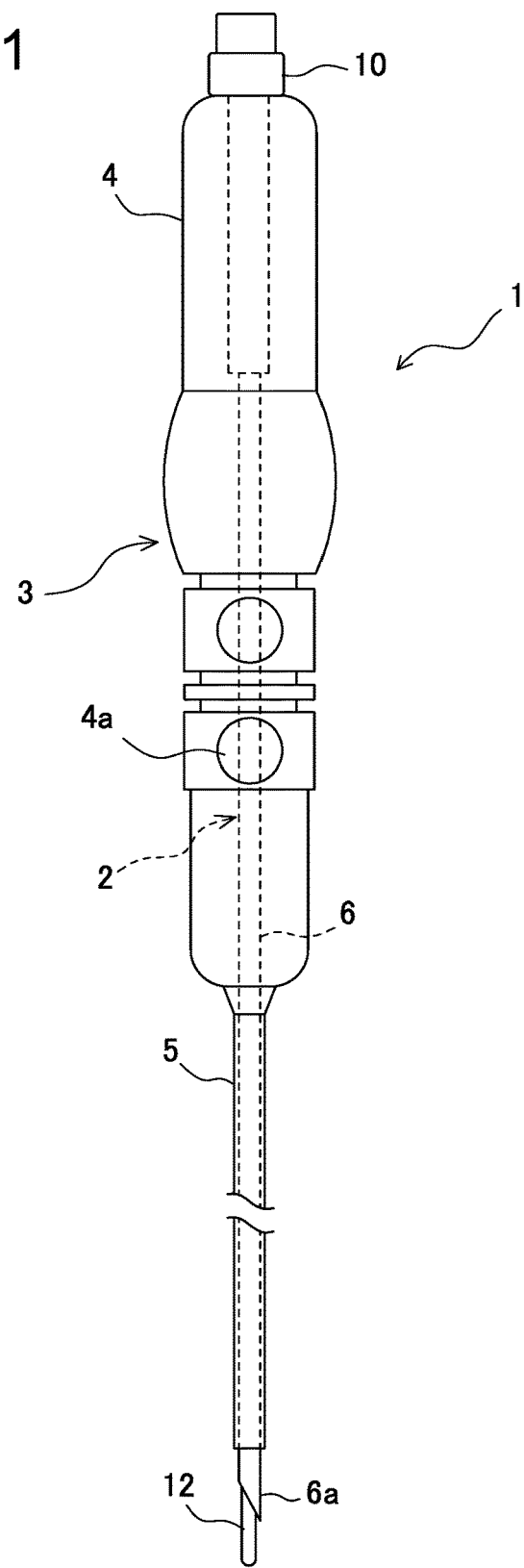
FIG. 1 is a front view illustrating a preferable embodiment of a biopsy needle device according to the present invention.

FIG. 1 illustrates a preferable embodiment of a biopsy needle device including a biopsy needle unit according to the present invention. A biopsy needle device 1 of the present embodiment is structured of a biopsy needle unit 2 and a main body portion 3 in which the biopsy needle unit 2 is integrated. The main body portion 3 is a typical example conventionally used in EUS-FNA and includes a handle portion 4 mounted on an ultrasonic endoscope device (not illustrated) and a sheath 5 inserted into an alimentary canal via the ultrasonic endoscope device.

Figure 2:
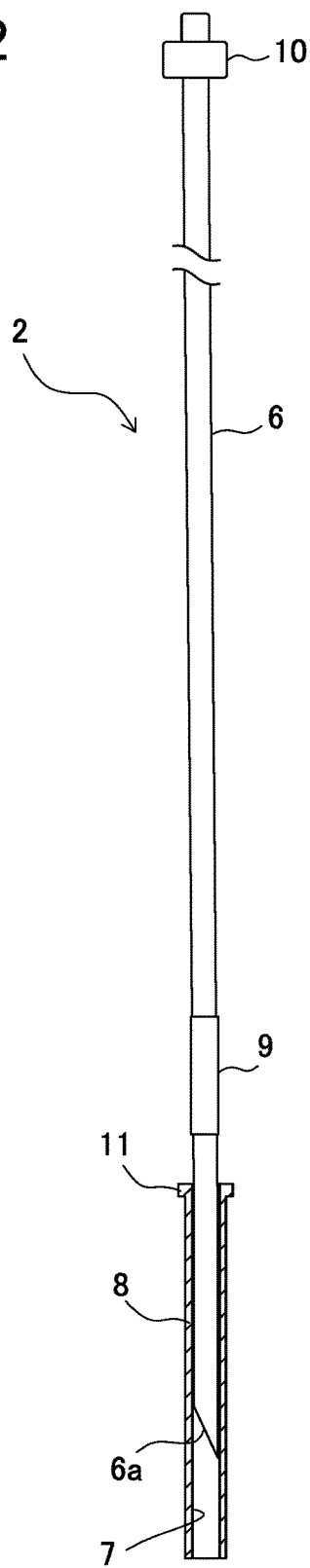
FIG. 2 is a front view illustrating a preferable embodiment of a biopsy needle unit according to the present invention.

FIG. 2 illustrates a preferable embodiment of a biopsy needle unit 2 according to the present invention. The biopsy needle unit 2 of the present embodiment is structured of a biopsy needle 6 formed of a needle tube having a sharp needle tip portion 6a at a tip and a safety tube 8 accommodating a lumen 7 through which the biopsy needle 6 is inserted along a longitudinal direction. As illustrated in FIG. 2, a marker 9 is arranged on the biopsy needle 6 at a position right above a position protruded from an upper end of the safety tube 8, that is, an end part on the opposite side to the needle tip portion 6a in a state that the needle tip portion 6a is completely accommodated in the lumen 7. A knob 10 for operation of the biopsy needle 6 is attached to a base end of the biopsy needle 6.

Figure 3:
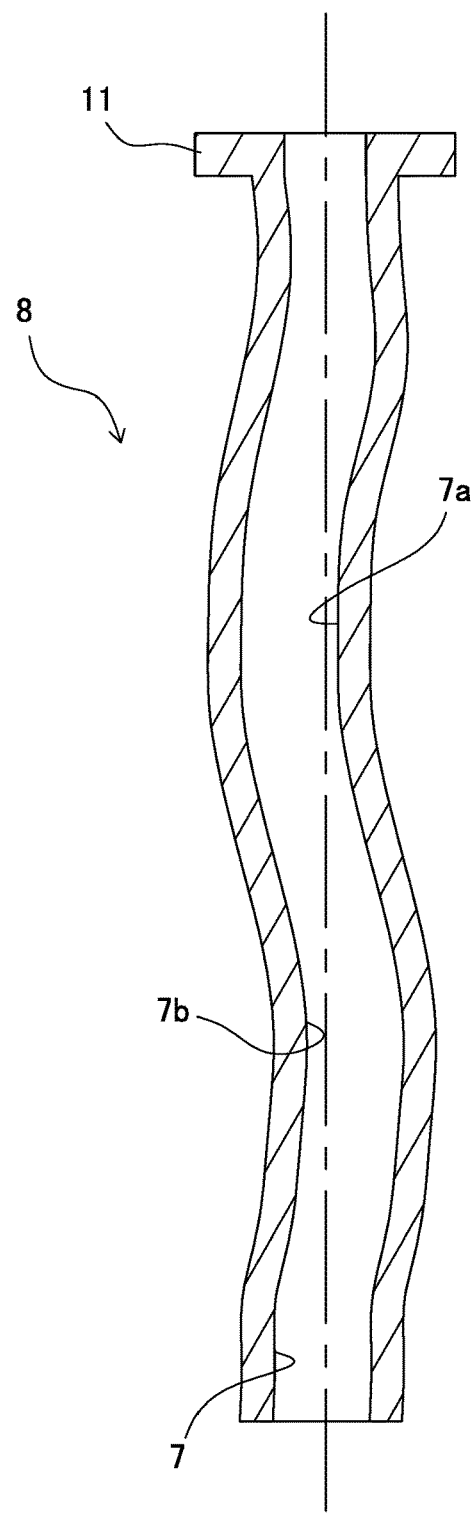
FIG. 3 is a longitudinal sectional view of a safety tube of FIG. 2.

The safety tube 8 is formed elastically deformable of a thermoplastic material, for example. As illustrated in FIG. 3, an external form of the safety tube 8 and the lumen 7 are curved with respect to the longitudinal direction approximately throughout the whole length. A flange portion 11 protruding outward in a radial direction is integrally formed at the upper end of the safety tube 8. Such a safety tube 8 can be formed with thermoplastic deformation of a tube member of a thermoplastic material including a lumen extending straight in the longitudinal direction, for example.

Figure 4:
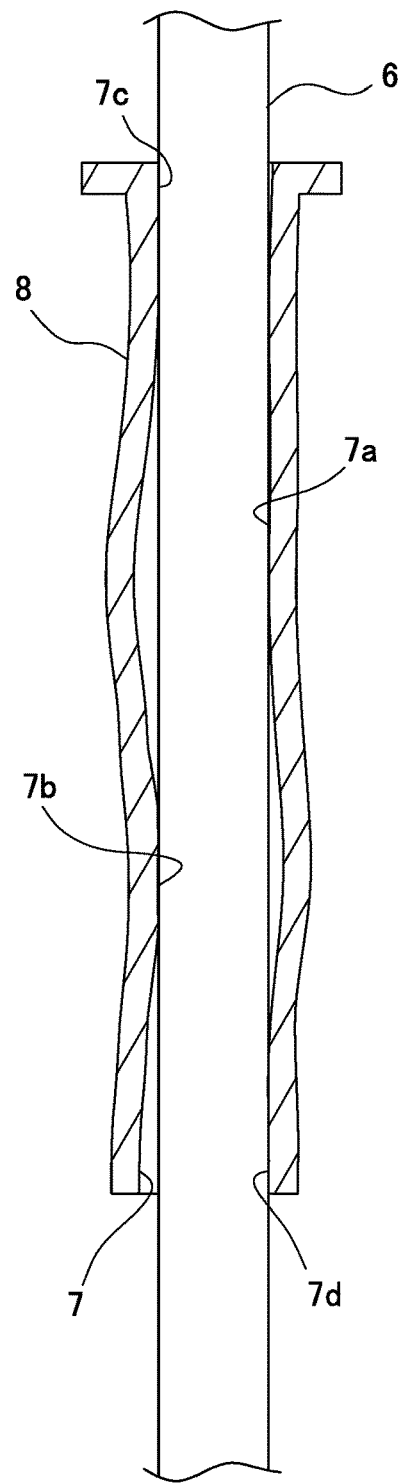
FIG. 4 is a longitudinal sectional view illustrating a state in which a biopsy needle is inserted to the safety tube of FIG. 3.

As illustrated in FIG. 4, when the biopsy needle 6 is inserted into the safety tube 8, an outer circumferential face thereof contacts to parts 7a, 7b of the lumen 7 protruding inward in the radial direction, so that the parts 7a, 7b are elastically deformed outward in the radial direction. In the illustrated embodiment, aperture edges 7c, 7d at both of upper and lower ends of the lumen 7 are contacted to the outer circumferential face of the biopsy needle 6 as well owing to reaction force from the contacting parts 7a, 7b of the lumen 7, so that the aperture edges 7c, 7d are elastically deformed outward in the radial direction.

Due to the contact between an inner circumferential face of the lumen 7 and the outer circumferential face of the biopsy needle 6, frictional resistance occurs therebetween. Owing to the frictional resistance, the safety tube 8 is held at the position without dropping from the biopsy needle 6 with gravitational force only by having the biopsy needle 6 be inserted to the safety tube 8 even without supporting of an operator with fingers or using a separate holding device. On the other hand, by supporting the safety tube 8 with a finger or a separate holding device, the biopsy needle 6 can be freely moved in the lumen 7 against the frictional resistance.

Next, description will be provided on usage of the biopsy needle unit 2 of the present embodiment. First, similarly to a conventional EUS-FNA, a stylet 12 is mounted, so that a tip thereof is partly protruded from the needle tip portion 6a, into a needle tube of the biopsy needle 6 from the upper end thereof having the safety tube 8 mounted so that the needle tip portion 6a is completely covered with the lumen 7. With the needle tip portion 6a being ahead, the above is inserted from an insertion port at an upper end of the handle portion 4 of the main body portion 3 and fixed to the handle portion 4 at a state in which the needle tip portion 6a and the tip of the stylet 12 are protruded from the sheath 5 by a predetermined length, as illustrated in FIG. 1. At this time, the safety tube 8 is held in the handle portion 4 with the flange portion 11 engaged with the aperture edge of the insertion port at the upper end of the handle portion 4.

In the biopsy needle device 1 of FIG. 1, length of the sheath 5 is adjusted by operating a sheath stopper 4a of the handle portion 4 and the needle tip portion 6a and the tip of the stylet 12 are accommodated in the sheath 5. Then, the biopsy needle device 1 is mounted on the ultrasonic endoscope device and the biopsy needle 6 is inserted to be located at a predetermined position in an alimentary canal while confirming an ultrasonic image. After pulling out the stylet 12, the handle portion 4 is operated to suck and collect biomedical tissue into the needle tube with the biopsy needle 6. Then, the knob 10 is operated to slightly pull out the biopsy needle 6 from the handle portion 4.

At this time, the safety tube 8 is pulled out from the insertion port at the upper end of the handle portion 4 together with the biopsy needle 6, as illustrated in FIG. 5A, due to frictional resistance between the inner circumferential face of the lumen 7 and the outer circumferential face of the biopsy needle 6. After the safety tube 8 is slightly pulled out, the biopsy needle 6 is further pulled out while holding the safety tube 8 with two fingers 13, for example.

When the marker 9 comes out from the upper end of the safety tube 8 as illustrated in FIG. 5B, the biopsy needle 6 is further pulled out with the fingers 13 released from the safety tube 8. Similarly, the safety tube 8 is pulled out from the handle portion 4 together with the biopsy needle 6 at a position where the marker 9 is exposed right outside from the upper end of the safety tube 8 due to frictional resistance between the inner circumferential face of the lumen 7 and the outer circumferential face of the biopsy needle 6.

At this time, as illustrated in FIG. 5B, the needle tip portion 6a of the biopsy needle 6 is completely accommodated in the lumen 7 of the safety tube 8. Accordingly, there is no risk to prick and hurt a body of a medical staff such as an operator and a caregiver or a patient, and safety is secured.

The biopsy needle unit according to the present invention can be applied to various biopsy needle devices of a commercially available luer connector type. Owing to the above, in a case that a sample is collected from different disorder areas of an identical patient, only the biopsy needle unit is required to be replaced and the whole of the biopsy needle device is not required to be replaced as conventionally. Accordingly, by replacing the biopsy needle unit while maintaining a tip position of the sheath in a body of a patient, sample collecting can be continuously performed rapidly and safely, and further, cost can be suppressed.

Figure 6:
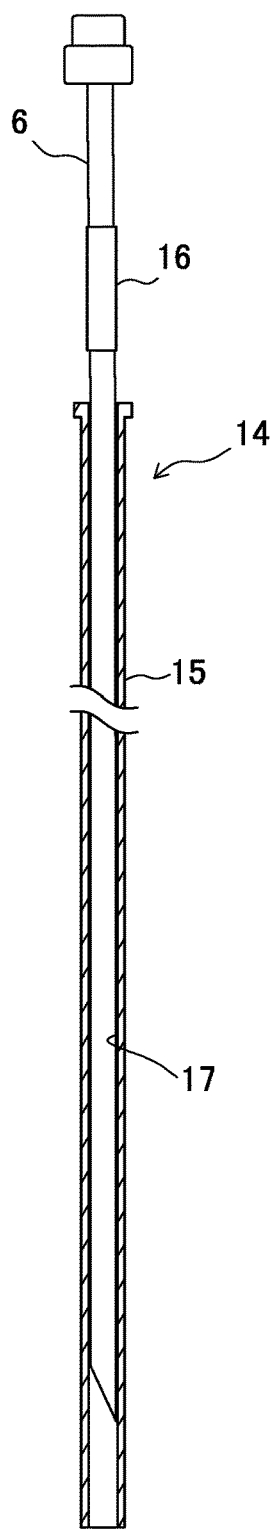
FIG. 6 is a front view illustrating a modified example of a biopsy needle unit.

FIG. 6 illustrates a modified example of a biopsy needle unit according to the present invention. A biopsy needle unit 14 of the modified example is different from the embodiment illustrated in FIG. 2 in that a safety tube 15 is longer than the safety tube 8 and that a marker 16 of the biopsy needle 6 is arranged at a base end side of the biopsy needle 6 in correspondence. Obviously, similarly to the embodiment illustrated in FIG. 2, an external form of the safety tube 15 and a lumen 17 formed therein are curved with respect to the longitudinal direction approximately throughout the whole length.

The long safety tube 15 of the present modified example is especially useful when the biopsy needle unit 2 mounted on the biopsy needle device 1 is replaced. The sheath 5 of the biopsy needle device 1 arranged in a body of a patient is not always straight but curved in many cases. In such a case, at the time of mounting a new biopsy needle unit 2, the biopsy needle 6 can proceed in the sheath 5 in a state that the needle tip portion 6a is accommodated in the safety tube 15. Accordingly, the needle tip portion 6a is protected from the inner surface of the sheath 5 with the safety tube 15 and inconvenience such as the needle tip portion 6a being caught and stuck in the inner surface of the sheath 5 can be prevented. On the contrary, the short safety tube 8 in FIG. 2 is suitable for a case in which the biopsy needle unit 2 is first integrated in the main body portion 3 before mounting onto the ultrasonic endoscope device. Thus, the length of the safety tube and the position of the marker can be set variously in accordance with usage, use conditions, and the like.

Figure 7:
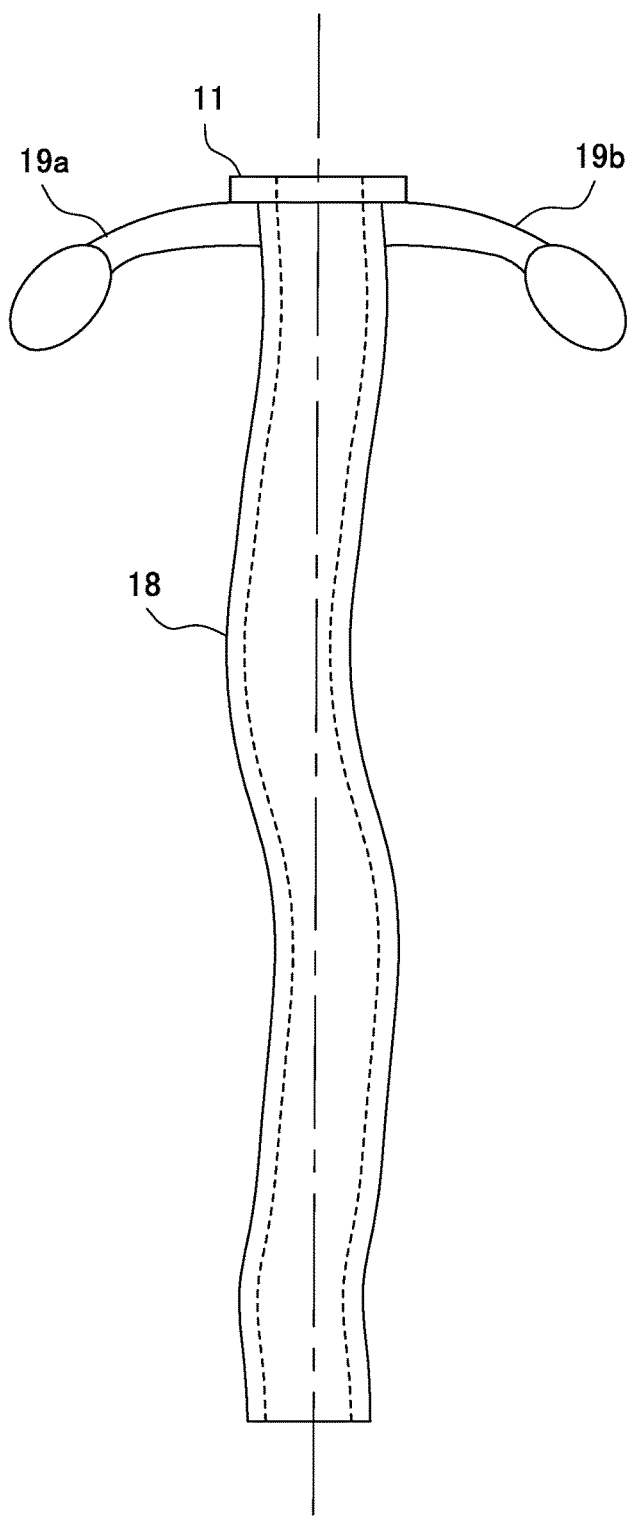
FIG. 7 is a front view illustrating a modified example of a safety tube.
Figure 8A:
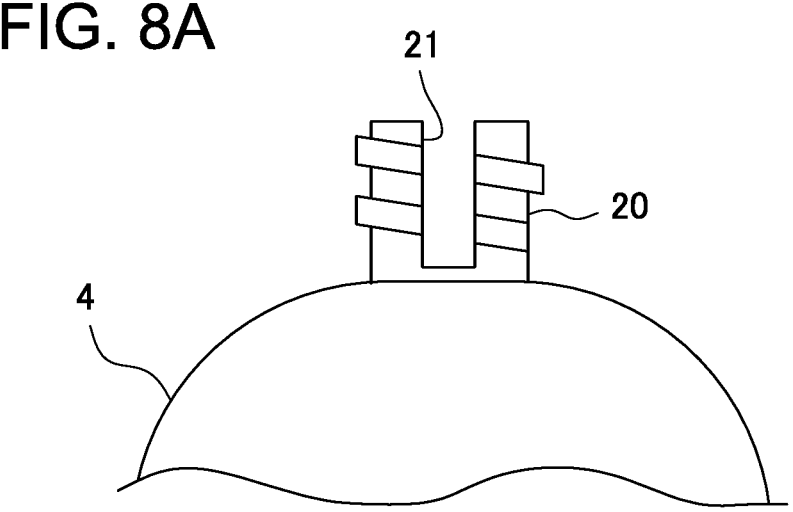
FIGS. 8A and 8B are partial enlarged views illustrating usage of the safety tube of FIG. 7.

FIG. 7 illustrates a modified example of the safety tube. A safety tube 18 of the modified example has, in addition to the flange portion 11 at the upper end, a right and left pair of narrow wing piece portions 19a, 19b integrally formed as being protruded further outward in the radial direction from the flange portion 11 and in mutually opposite directions. In this case, as illustrated in FIG. 8A, at the upper end of the handle portion 4 of the main body portion 3, a groove 21 opened upward having width corresponding to the wing piece portions 19a, 19b is formed on a hub 20 to screw and fix the knob 10 of the biopsy needle 6 inserted to the insertion port.

Figure 8B:
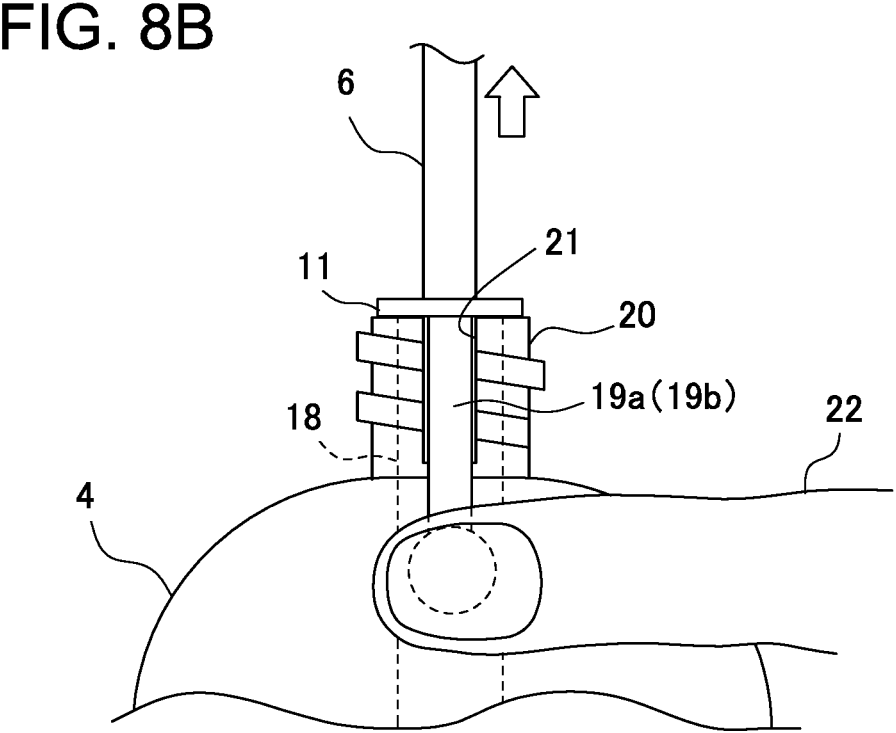

At the time of using, the wing piece portions 19a, 19b are fitted in the groove 21 of the hub 20 so that the safety tube 18 is held at the upper end of the handle portion 4. When pulling out the biopsy needle 6 from the handle portion 4, as illustrated in FIG. 8B, the wing piece portions 19a, 19b are held with two fingers 22 until the marker 9 comes out from the upper end of the safety tube 18. Thus, the safety tube 18 can be held more easily.

FIGS. 9A and 9B illustrate a handle portion 23 including a holding mechanism capable of pulling out the biopsy needle 6 together with the safety tube 8 in a state that the needle tip portion 6a is completely accommodated in the lumen 7 without holding the safety tube 8 with fingers. The holding mechanism is structured of a needle stopper 24 and a holding portion 25 arranged inside the handle portion 23.

The needle stopper 24 is extended displaceable in a horizontal direction in the handle portion 23. One end of the needle stopper 24 penetrates a side wall of the handle portion 23 and is arranged at the outside thereof. Further, the needle stopper 24 includes a needle insertion hole 26 opened relatively largely in a vertical direction. The needle stopper 24 is continuously urged outward in the horizontal direction by a spring 27 at the other end side.

The holding portion 25 is arranged being protruded toward the biopsy needle 6 and the safety tube 8 from the inner wall of the handle portion 23 on the opposite side to the spring 27 across the biopsy needle 6 and the safety tube 8 vertically penetrating the approximate center of the handle portion 23. The holding portion 25 is arranged below the needle stopper 24 at a height facing the outer circumferential face of the safety tube 8.

Alignment of the needle insertion hole 26 is performed by pushing an operation button 24a of the needle stopper 24 from the outside of the handle portion 23, and the biopsy needle 6 and the safety tube 8 are inserted to the needle insertion hole 26 after performing positioning of the needle insertion hole 26. When the operation button 24a is released after the biopsy needle unit 2 is fixed to the handle portion 23, the needle stopper 24 is urged outward by the spring 27 and displaced to the left side in FIGS. 9A and 9B. Then, as illustrated in FIG. 9A, the inner circumferential face 26a of the needle insertion hole 26 is contacted to the outer circumferential face of the safety tube 8 facing thereto at the spring 27 side, and concurrently, the outer circumferential face of the safety tube 8 is contacted to the end face 25a of the holding portion 25 facing thereto on the opposite side to the spring 27.

Thus, the safety tube 8 is held, being sandwiched from both sides, at a position being vertically apart along the axial direction with the needle insertion inner circumferential face 26a and the holding portion end face 25a. Due to urging force of the spring 27, frictional resistance is generated between the outer circumferential face of the engaged safety tube 8 and the needle insertion hole inner circumferential face 26a and between the outer circumference face of the engaged safety tube 8 and the holding portion end face 25a. Accordingly, even when the biopsy needle 6 is moved in a direction to be pulled out from the handle portion 23, the safety tube 8 is held in the handle portion 23 without being pulled out together therewith.

For pulling out the biopsy needle 6, the operation button 24a of the needle stopper 24 is depressed after the marker 9 comes out from the upper end of the safety tube 8. According to the above, the safety tube 8 is released from the engaging state with the needle insertion hole inner circumferential face 26a and the holding portion end face 25a and frictional resistance therewith vanishes. Accordingly, as illustrated in FIG. 9B, the safety tube 8 can be pulled out from the handle portion 23 together with the biopsy needle 6. At this time, since the needle tip portion 6a of the biopsy needle 6 is completely accommodated in the lumen 7 of the safety tube 8, there is no risk to prick and hurt a body of a medical staff such as an operator and a caregiver and a patient, and safety is secured.

Figure 10:
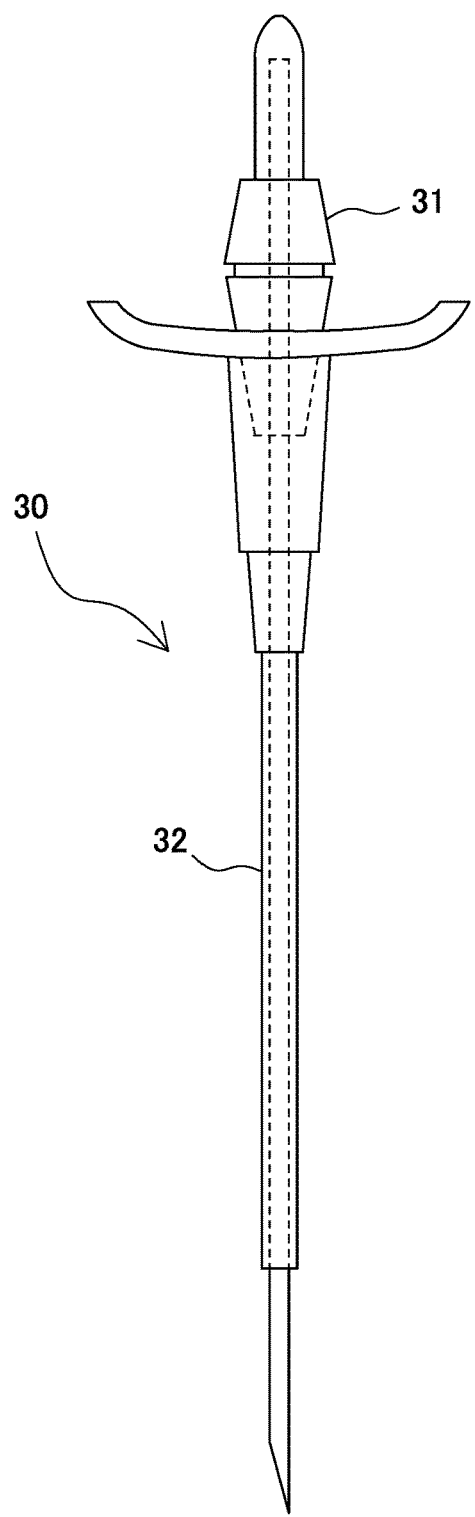
FIG. 10 is a front view illustrating a preferable embodiment of a blood sampling needle unit according to the present invention.
Figure 11A:
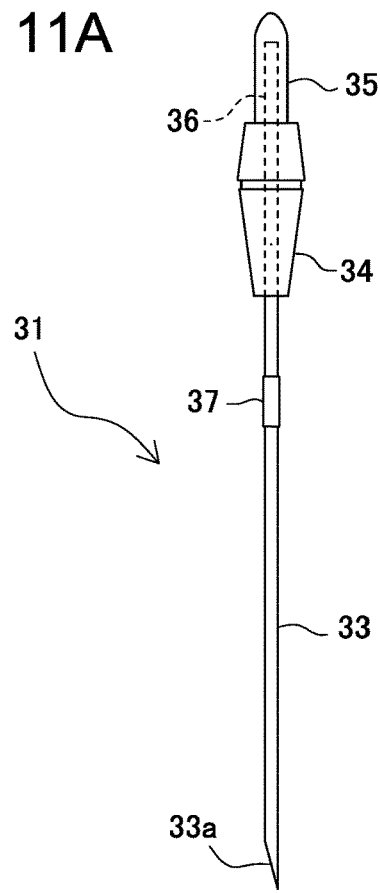
FIG. 11A is a front view of a blood sampling needle of FIG. 10

FIG. 10 illustrates a preferable embodiment of a blood sampling needle unit according to the present invention. A blood sampling needle unit 30 of the present embodiment is structured of a blood sampling needle 31 and a safety tube 32 outwardly inserted to the blood sampling needle 31. As illustrated in FIG. 11A, the blood sampling needle 31 basically has a conventionally known general structure and includes a needle tube 33 having a sharp needle tip portion 33a at a distal end thereof, a needle hub 34 at a base end of the needle tube 33, and a needle 36 extended to the opposite side from the needle hub 34 and covered in a rubber sleeve 35. The blood sampling needle 31 of the present embodiment further includes a marker 37 arranged at a predetermined position on the needle tube 33.

Figure 11B:
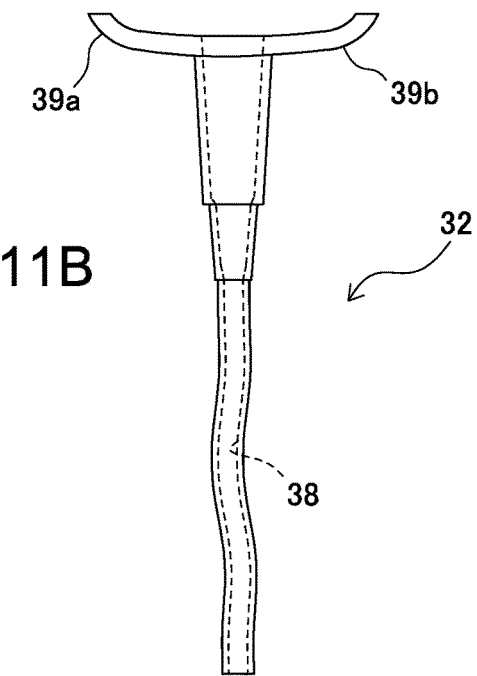
FIG. 11B is a front view of a safety tube of FIG. 10.

The safety tube 32 is formed elastically deformable of a thermoplastic material, for example. As illustrated in FIG. 11B, the safety tube 32 has a lumen 38, at the inside thereof, through which the needle tube 33 of the blood sampling needle 31 is inserted with respect to the longitudinal direction. The marker 37 of the blood sampling needle 31 is arranged at a position right above a position protruded from an upper end of the safety tube 32 in a state that the needle tip portion 33a of the needle tube 33 is completely accommodated in the lumen 38. A right and left pair of narrow wing piece portions 39a, 39b protruded outward in the radial direction and in mutually opposite directions is integrally formed at the upper end of the safety tube 32.

The safety tube 32 and the lumen 38 are curved with respect to the longitudinal direction approximately throughout the whole length. Therefore, a part protruding inward in the radial direction is formed in the lumen 38. As described above with reference to FIG. 4, when the needle tube 33 is inserted to the safety tube 32, the protruding part in the lumen 38 contacts to the outer circumferential face thereof and is elastically deformed outward in the radial direction.

At this time, owing to the frictional resistance generated between the inner circumferential face of the lumen 38 and the outer circumferential face of the needle tube 33, the safety tube 32 is held at the position without dropping from the needle tube 33 with gravitational force only by having the needle tube 33 be inserted to the safety tube 32 even without supporting of an operator with fingers or using a separate holding device. Similarly to the safety tube 8 of FIG. 3, such a safety tube 32 can be formed by thermoplastic deformation of a tube member of a thermoplastic material including a lumen extending straight in the longitudinal direction, for example.

FIGS. 12A to 12C exemplify usage of the blood sampling needle unit 30. Similarly to a general blood sampling needle, in the blood sampling needle unit 30, a blood sampling holder 40 is fixedly mounted on the needle hub 34 on the needle 36 side. Next, as illustrated in FIG. 12A, the needle tube 33 is stuck to a blood vessel from a surface of a skin 41. At this time, it is preferable to partially insert the safety tube 32 to subcutaneous tissue. In another example, the distal end of the safety tube 32 can be stuck to stop at the surface of the skin 41. When blood flows into the rubber sleeve 35, a vacuum blood sampling tube 42 is mounted on a blood sampling holder 42 and blood sampling is performed.

When blood sampling is finished, the vacuum blood sampling tube 42 is removed from the blood sampling holder 40, and then, pulling out of the blood sampling needle 31 is started while holding the wing piece portions 39a, 39b of the safety tube 32 with two fingers 43, for example, as illustrated in FIG. 12B. When the marker 38 comes out from the upper end of the safety tube 32, the biopsy needle 31 is further pulled out with the fingers 43 released from the wing piece portions 39a, 39b. Due to frictional resistance between the inner circumferential face of the lumen 38 and the outer circumferential face of the needle tube 33, the safety tube 32 is removed together with the needle tube 33.

At this time, as illustrated in FIG. 12C, the needle tip portion 33a of the needle tube 33 is completely accommodated in the lumen 38 of the safety tube 32. Accordingly, there is no risk to prick and hurt a body of a medical staff such as an operator and a caregiver or a patient, and safety is secured.

Figure 13:
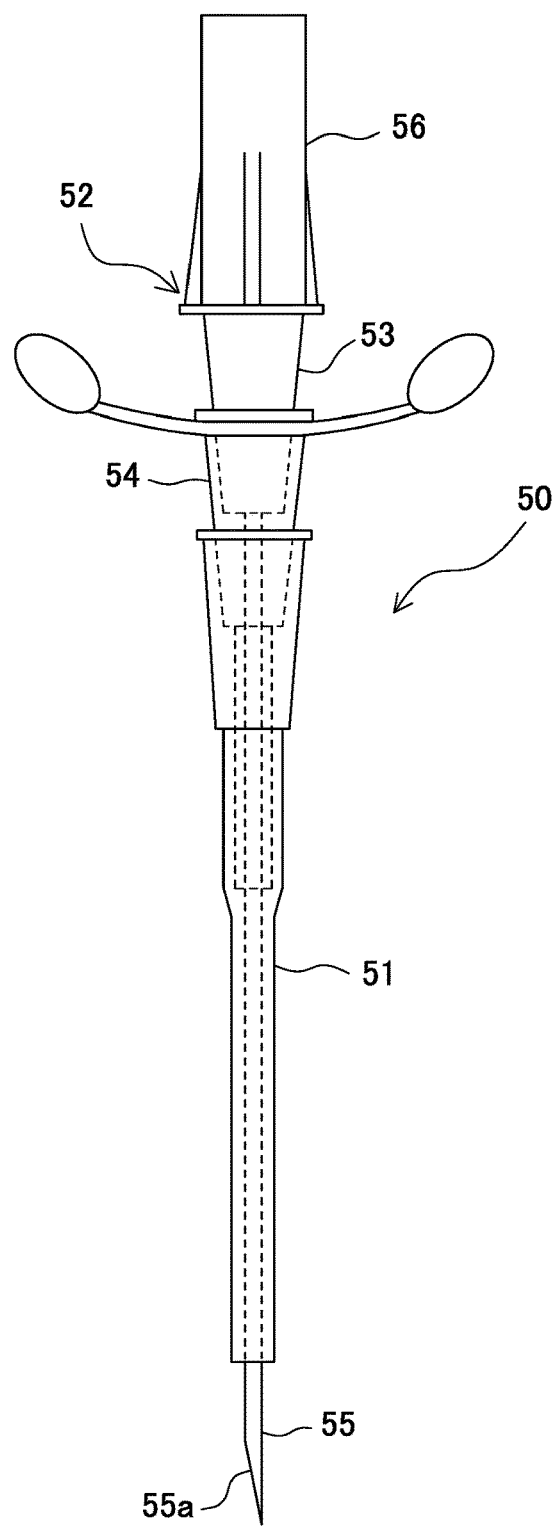
FIG. 13 is a front view illustrating a preferable embodiment of a puncture needle system for blood access according to the present invention.
Figure 14A:
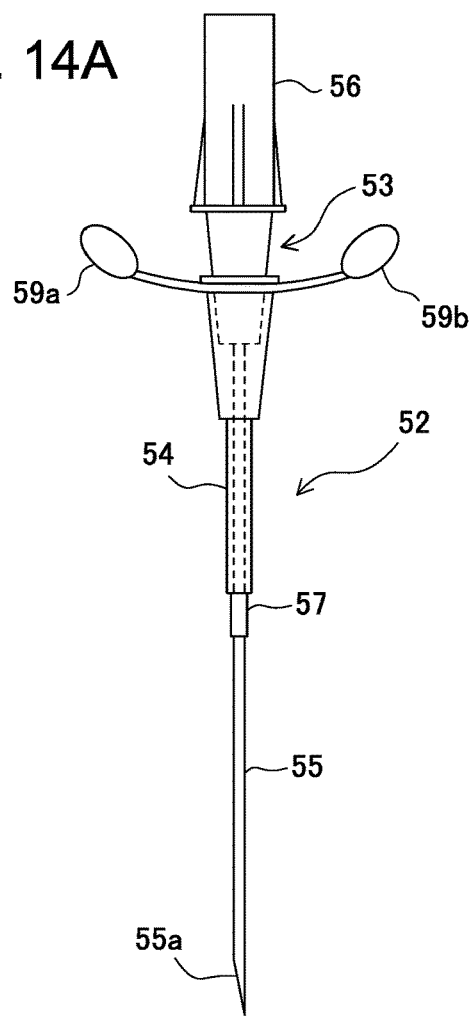
FIG. 14A is a front view of a puncture needle unit of FIG. 13

FIG. 13 illustrates a preferable embodiment of a puncture needle system for blood access according to the present invention. A puncture needle system 50 of the present embodiment is structured of a catheter 51 for blood access and a puncture needle unit 52 for blood access inserted in the catheter 51. As illustrated in FIG. 14A, the puncture needle unit 52 is structured of a puncture needle 53 and a safety tube 54 outwardly inserted to the puncture needle 53.

Figure 15A:
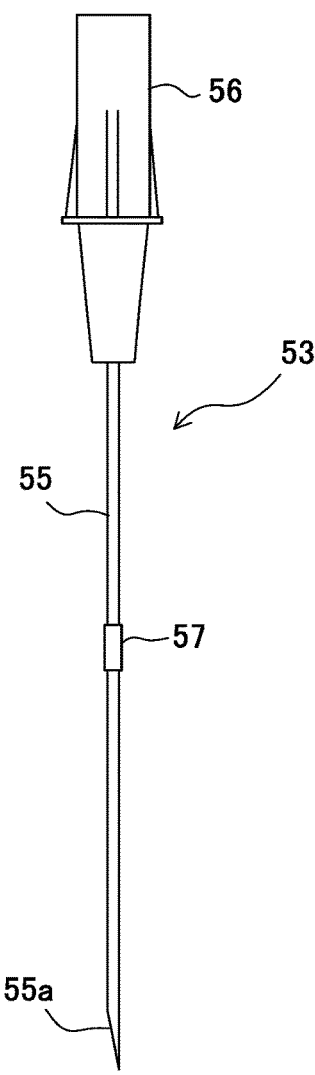
FIG. 15A is a front view of a puncture needle of FIG. 14A

As illustrated in FIG. 15A, the puncture needle 53 basically has a conventionally known general structure and includes an inner needle 55 structured of needle tube having a sharp needle tip portion 55a at a distal end thereof, and a hub 56 arranged at a base end of the inner needle 55. The puncture needle 53 of the present embodiment further includes a marker 57 arranged at a predetermined position on the inner needle 55.

Figure 15B:
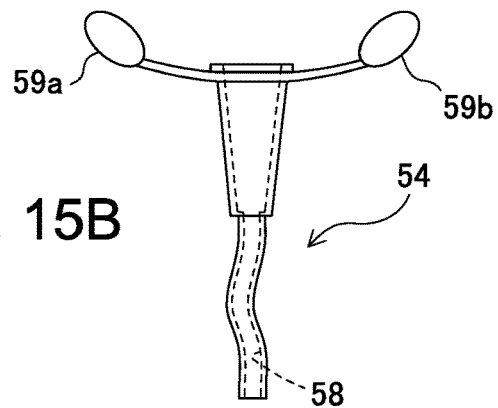
FIG. 15B is a front view of a safety tube of FIG. 14A.

The safety tube 54 is formed elastically deformable of a thermoplastic material, for example. As illustrated in FIG. 15B, the safety tube 54 has a lumen 58, at the inside thereof, through which the inner needle 55 of the puncture needle 53 is inserted along the longitudinal direction. The marker 57 of the puncture needle 53 is arranged at a position right above a position protruded from an upper end of the safety tube 54 in a state that the needle tip portion 55a of the inner needle 55 is completely accommodated in the lumen 58. A right and left pair of narrow wing piece portions 59a, 59b protruded outward in the radial direction and in mutually opposite directions is integrally formed at the upper end of the safety tube 54.

The safety tube 54 and the lumen 58 are curved with respect to the longitudinal direction approximately throughout the whole length. Therefore, a part protruding inward in the radial direction is formed in the lumen 58. As described above with reference to FIG. 4, when the inner needle 55 is inserted to the safety tube 54, the protruding part in the lumen 38 contacts to the outer circumferential face thereof and is elastically deformed outward in the radial direction.

At this time, owing to the frictional resistance generated between the inner circumferential face of the lumen 58 and the outer circumferential face of the inner needle 55, the safety tube 54 is held at the position without dropping from the inner needle 55 with gravitational force only by having the inner needle 55 be inserted to the safety tube 54 even without supporting of an operator with fingers or using a separate holding device. Similarly to the safety tube 8 of FIG. 3, such a safety tube 54 can be formed by thermoplastic deformation of a tube member of a thermoplastic material including a lumen extending straight in the longitudinal direction, for example.

As illustrated in FIG. 14A, the puncture needle unit 52 is used with the puncture needle 53 inserted to the safety tube 54 to a position where the upper end portion of the safety tube 54 covers the base end portion of the inner needle 55. The catheter 51 is outwardly inserted onto the safety tube 54 mounted on the puncture needle unit 52 as described above. As illustrated in FIG. 13, the catheter 51 is mounted so that the needle tip portion 55a is exposed from the inner needle 55 from the distal end thereof similarly to a general puncture needle for blood access.

Figure 14B:
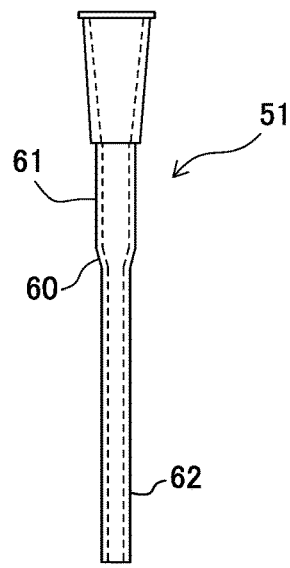
FIG. 14B is a front view of a catheter of FIG. 13.

As illustrated in FIG. 14B, the catheter 51 of the present embodiment includes a large-diameter portion 61 at the base end side and a small-diameter portion 62 at the distal end side via a step 60. The large-diameter portion 61 is formed so that an external form thereof and the lumen corresponds to an external form and dimensions of the safety tube 54 which is outwardly inserted to the inner needle 55. The small-diameter portion 62 is formed corresponding to dimensions of the inner needle 55. In another example, the step 60 between the large-diameter portion 61 and the small-diameter portion 62 may be eliminated to be formed smoothly and continuously.

FIGS. 16A and 16B exemplify usage of the puncture needle system 50 for blood access. Similarly to a general puncture needle for blood access, a syringe 63 is connected to the hub 56 in the puncture needle system 50 for blood access. Next, as illustrated in FIG. 16A, the inner needle 55 and the catheter 51 are stuck to the surface of a skin 64 and are inserted to a blood vessel. After blood flows into the syringe 63, the puncture needle unit 52 is removed while retaining the catheter 51.

At that time, pulling-out of the inner needle 55 is started while holding the wing piece portions 59a, 59b of the safety tube 54 with two fingers 65, for example, as illustrated with an imaginary line in FIG. 16B. When the marker 57 comes out from the upper end of the safety tube 54, the fingers 65 are released from the wing piece portions 59a, 59b and the inner needle 55 is further pulled out. Due to frictional resistance between the inner circumferential face of the lumen 58 and the outer circumferential face of the inner needle 55, the safety tube 54 is removed together with the inner needle 55.

At this time, as illustrated in FIG. 16B, the needle tip portion 55a of the inner needle 55 is completely accommodated in the lumen 58 of the safety tube 54. Accordingly, there is no risk to prick and hurt a body of a medical staff such as an operator and a caregiver or a patient, and safety is secured.

In the above, the present invention is described in detail based on preferable embodiments. Here, various changes and modifications can be applied to the embodiments described above within the technical scope of the present invention. For example, the puncture needle unit of the present invention may have various known structures not limited to the above embodiments. Further, the safety tube of the present invention may be applied to various other puncture needles and puncture needle devices not limited to the biopsy needle, blood sampling needle, and puncture needle for blood access of the above embodiments. Further, the wing piece portions of the safety tube of FIGS. 11B and 15B can be eliminated. In such a case, the blood sampling needle or the puncture needle may be pulled out while holding the upper end portion of the safety tube from both sides with fingers.

EXPLANATION OF REFERENCES

1 Biopsy needle device
2, 14 Biopsy needle unit
3 Main body portion
4 Handle portion
5 Sheath
Biopsy needle
6a, 33a, 55a Needle tip portion
7, 17, 38, 58 Lumen
8, 15, 18, 32, 54 Safety tube
9, 16, 37, 57 Marker
10 Knob
11 Flange portion
12 Stylet
13, 22, 43, 65 Finger
19a, 19b, 39a, 39b, 59a, 59b Wing piece portion
20, 56 Hub
21 Groove
22 Handle portion
23 Needle stopper
24a Operation button
26 Needle insertion hole
26a Inner circumferential face
27 Spring
30 Blood sampling needle unit
31 Blood sampling needle
33 Needle tube
34 Needle hub
35 Rubber sleeve
36 Needle
40 Blood sampling holder
41, 64 Skin
42 Vacuum blood sampling tube
50 Puncture needle system
51 Catheter for blood access
52 Puncture needle unit
53 Puncture needle
55 Inner needle
60 Step
61 Large-diameter portion
62 Small-diameter portion
63 Syringe

The invention claimed is:

1. A puncture needle unit, comprising:
a puncture needle; and
a safety tube including a lumen which extends throughout a whole length in a longitudinal direction and being capable of elastically deforming to partially cover the puncture needle inserted to the lumen,
wherein the puncture needle includes a needle tube having a marker arranged at a position protruding from an end portion of the safety tube on an opposite side to a needle tip of the puncture needle when the needle tip is accommodated in the lumen, and
the lumen is curved at least partially with respect to the longitudinal direction so that the safety tube is elastically deformed due to contact between an inner circumferential face of the lumen and an outer circumferential face of the needle tube when the puncture needle is inserted to the lumen to cause frictional resistance between the inner circumferential face of the lumen and the outer circumferential face of the needle tube.

2. The puncture needle unit according to claim 1, wherein the safety tube is formed, by thermoplastic deformation, of a tube member of a thermoplastic material including the lumen extending straight in the longitudinal direction.

3. The puncture needle unit according to claim 1, wherein the safety tube has a protruding portion protruded outward in a radial direction at the end portion on the opposite side to the needle tip of the puncture needle inserted to the lumen.

4. The puncture needle unit according to claim 1, wherein the puncture needle is a biopsy needle.

5. The puncture needle unit according to claim 1, wherein the puncture needle is a blood sampling needle.

6. The puncture needle unit according to claim 1, wherein the puncture needle is a puncture needle for blood access.

7. A puncture needle device comprising:
the puncture needle unit for biopsy according to claim 3 and a main body portion to which the puncture needle unit is assembled,
wherein the main body portion includes a sheath to which the puncture needle is inserted, and a handle portion which holds the safety tube at a predetermined position when the puncture needle is inserted to the sheath.

* * * * *